(12) United States Patent
Wolfowitz

(10) Patent No.: US 9,243,264 B2
(45) Date of Patent: Jan. 26, 2016

(54) PRODUCTION OF METHANE

(71) Applicant: FFGF LIMITED, Tortola (VG)

(72) Inventor: Steven Alan Wolfowitz, Rossburgh (ZA)

(73) Assignee: FFGF Limited, Tortola (VG)

( * ) Notice: Subject to any disclaimer, the term of this patent is extended or adjusted under 35 U.S.C. 154(b) by 0 days.

(21) Appl. No.: 14/417,398

(22) PCT Filed: Jul. 29, 2013

(86) PCT No.: PCT/IB2013/056215
§ 371 (c)(1),
(2) Date: Jan. 26, 2015

(87) PCT Pub. No.: WO2014/016815
PCT Pub. Date: Jan. 30, 2014

(65) Prior Publication Data
US 2015/0176030 A1 Jun. 25, 2015

(30) Foreign Application Priority Data

Jul. 27, 2012 (ZA) .................................. 2012/05680
Sep. 14, 2012 (ZA) .................................. 2012/06901

(51) Int. Cl.
| | | |
|---|---|---|
| C12M 1/42 | (2006.01) | |
| C12M 1/107 | (2006.01) | |
| C12N 1/20 | (2006.01) | |
| C12N 13/00 | (2006.01) | |
| C12P 5/02 | (2006.01) | |
| C25B 1/02 | (2006.01) | |
| C25B 3/04 | (2006.01) | |
| C25B 9/00 | (2006.01) | |
| C25B 15/02 | (2006.01) | |
| C25B 15/08 | (2006.01) | |

(52) U.S. Cl.
CPC ................ *C12P 5/023* (2013.01); *C12M 21/04* (2013.01); *C12M 35/02* (2013.01); *C12M 35/04* (2013.01); *C12N 1/20* (2013.01); *C12N 13/00* (2013.01); *C25B 1/02* (2013.01); *C25B 3/04* (2013.01); *C25B 9/00* (2013.01); *C25B 15/02* (2013.01); *C25B 15/08* (2013.01); *Y02E 50/343* (2013.01)

(58) Field of Classification Search
CPC ........ C02F 11/04; C02F 3/28; C02F 2103/20; C02F 3/34; C02F 2103/28; C02F 2209/02; C02F 2209/03; C02F 2209/42; C02F 2301/066; C02F 11/185; C02F 1/20; C02F 1/34; C02F 1/56; C02F 1/66; C02F 2103/22
See application file for complete search history.

(56) References Cited

U.S. PATENT DOCUMENTS

| | | | |
|---|---|---|---|
| 4,540,666 | A | 9/1985 | Nukina et al. |
| 4,571,384 | A | 2/1986 | Morita et al. |
| 4,883,753 | A | 11/1989 | Belaich et al. |
| 2006/0011491 | A1 | 1/2006 | Logan et al. |
| 2009/0317882 | A1 | 12/2009 | Cheng et al. |
| 2011/0165667 | A1 | 7/2011 | Mets |
| 2011/0300411 | A1 | 12/2011 | Materi |

FOREIGN PATENT DOCUMENTS

| | | |
|---|---|---|
| DE | 10 2011 015 415 A1 | 10/2012 |
| EP | 1 574 581 A2 | 9/2005 |
| GB | 2476090 | 6/2011 |
| WO | WO 2005-005981 A2 | 1/2005 |
| WO | WO 2008-094282 A1 | 8/2008 |
| WO | WO 2009-072887 A1 | 6/2009 |
| WO | WO 2010-007602 A1 | 1/2010 |
| WO | WO 2010-147683 A1 | 12/2010 |
| WO | WO 2011-000084 A1 | 1/2011 |
| WO | WO 2011-003081 A1 | 1/2011 |
| WO | WO 2011-055322 A1 | 5/2011 |
| WO | WO 2012-110256 A1 | 8/2012 |
| WO | WO 2012-110257 A1 | 8/2012 |
| WO | WO 2012-158941 A2 | 11/2012 |
| WO | WO 2013-060331 A1 | 5/2013 |

OTHER PUBLICATIONS

Miller, Jay F., et al. "Pressure and Temperature Effects on Growth and Methane Production of the Extreme Thermophile Methanococcus jannaschii." Applied and Environmental Microbiology, vol. 54, No. 12, Sep. 26, 1988, pp. 3039-3042.
Cheng et al., "Direct Biological Conversion of Electrical Current Into Methane by Electromethanogenesis", Environmental Science & Technology, American Chemical Society, vol. 43, No. 10, Mar. 26, 2009, pp. 3953-3958.
International Search Report for PCT/IB2013/056215, Dated May 27, 2014.

*Primary Examiner* — Debbie K Ware
(74) *Attorney, Agent, or Firm* — Nixon Peabody LLP; Jeffrey L. Costellia

(57) ABSTRACT

This invention relates to a method for producing hydrocarbons from carbon dioxide and water in the presence of hydrogen and methanogen/s, the methanogen/s is/are provided in an aqueous growth substrate and the aqueous growth substrate is pressurized to a pressure of from 5 to 1000 bar with a pressurizing fluid containing or comprising carbon dioxide. In an embodiment of the invention, a cathode is provided to generate hydrogen and also to control the pH of the aqueous growth substrate. The invention also relates to an apparatus for carrying out the method.

41 Claims, 9 Drawing Sheets

PRODUCTION OF METHANE

BACKGROUND OF THE INVENTION

The planet Earth is currently plagued by two major problems having severe effects on it and its inhabitants, namely:
   global warming resulting from excessive carbon dioxide production; and
   excessively high crude oil and consequently high petrol and diesel prices.

An object of this invention is to reduce these problems.

The increase in production of fossil fuel utilizing engines has resulted in excessive demand for crude oil in turn resulting in excessively high prices. The consumption of these fuels and that by oil, gas and coal-fired power stations, etc., has increased the amount of carbon dioxide produced which has led to global warming. The absorbtion of carbon dioxide by trees and resulting release of oxygen has been debilitated by the removal of extensive forests. This imbalance has thrown and continues to cumulatively throw the world's ecology out of kilter.

Efforts to improve efficiencies of engines and reduce wastage of fossil fuel products have little chance of improving the situation because of exponentially growing populations and their aspirations. Other technologies are actively being sought.

Ways to address the problems mentioned above include:
   reduction of carbon dioxide in the atmosphere;
   reduction of 'carbon footprint' (the use of carbon products); and
   reduction of demand for crude oil and other fossil fuels (resulting in a decrease in their prices, by finding replacements).

It is an object of this invention to provide a method and apparatus which contributes to the above reductions and further provides for the production of methane.

SUMMARY OF THE INVENTION

This invention relates to a method for producing hydrocarbons from carbon dioxide and water in the presence of hydrogen and methanogen/s, wherein the methanogen/s is/are provided in an aqueous growth substrate and the aqueous growth substrate is pressurized to a pressure of from 5 to 1000 bar, typically from 5 to 500 bar, preferably from 5 to 200 bar, more preferably from 10 to 150 bar, more preferably from 20 to 150 bar, most preferably from 40 to 150 bar with a pressurizing fluid containing or comprising carbon dioxide.

Preferably, the method is carried out in a reaction vessel in which sufficient aqueous growth substrate is provided to provide an aqueous growth substrate to head space volumetric ratio of 1:1 to 3:1, typically a volumetric ratio from 2:1 to 3:1.

The aqueous growth substrate may be pressurized with a mixture of hydrogen and carbon dioxide which may be present in a molar ratio of 4:1 to 1:4, from 2:1 to 1:4, from greater than 1:1 to 1:4 or even from 1:2 to 1:4.

The pH of the aqueous growth medium is preferably maintained in the range from 6 to 7.5, preferably 6.5 to 7.

The methanogen/s may be anaerobic Archaea, which may be a hyperthermophilic hyperextremophile or, psychrophile/cryophile and/or an exoelectrogenic microbiological organism.

The method is carried out at a temperature at or near the optimum for growth of the methanogen/s.

In the case where the methanogen/s is/are a hyperthermophilic hyperextremophife anaerobic Archaea, the reaction vessel may be operated at a temperature of 50° C. to 400° C., preferably 80° C. to 200° C., more preferably 80° C. to 150° C.

In the case where the methanogen/s is/are a psychrophile/cryophile anaerobic Archaea, the reaction vessel may be operated at a temperature of −50 to 50° C., preferably −5 to −20° C., most preferably about −15° C.

Preferably, the pH of the aqueous growth medium is controlled.

The pH of the aqueous growth medium may be controlled by providing a cathode in the reaction vessel and passing a current through the aqueous growth medium to generate hydrogen and also to control the pH.

According to preferred embodiment of the invention, a method for the production of methane from carbon dioxide and water in the presence of hydrogen and methanogen/s includes the steps of:
   a) providing an anode reaction vessel (14) containing a positive electrode (anode) and a liquid electrolytic medium comprising water and ionizing material;
   b) providing a cathode reaction vessel (12) containing a negative electrode (cathode), an electrolytic aqueous growth substrate, methanogen/s and carbon dioxide;
   c) connecting the first and second reaction vessels with connection means which allows electrons and/or ions, to pass between the electrolytic media of the anode and cathode reaction vessels;
   d) applying a direct electrical current to the positive electrode and the negative electrode to:
      effect ionization of hydrogen in the cathode reaction vessel (12) to produce hydrogen and also to increase the pH of the electrolytic aqueous growth substrate; and
      effect ionized oxygen in the first reaction vessel (14), to form oxygen.

Methane is recovered from the cathode reaction vessel (12).

Oxygen is recovered from the first reaction vessel (14).

The reaction vessels (12) and (14) are operated at the same internal pressure, and may be operated at different temperatures.

The connection means is preferably an electrolytic medium, in which case a membrane which allows electrons to pass through, and possibly some ions, is be provided.

Preferably, the connection means is provided with a valve that is insulated from the electrolyte.

The reaction vessels may be operated under different conditions, for example the anode reaction vessel (14) may be operated at ambient temperature at about 25° C.; and the cathode reaction vessel (12) may be operated at a temperature at or near the optimum for growth of the methanogen/s.

In the case where the methanogen/s is/are a hyperthermophilic hyperextremophile anaerobic Archaea, the cathode reaction vessel (12) may be operated at a temperature of 50° C. to 400° C., preferably 80° C. to 200° C., more preferably 80° C. to 150° C.

In the case where the methanogen/s is/are a psychrophile/cryophile anaerobic Archaea, the cathode reaction vessel (12) may be operated at a temperature of −50 to 50° C., preferably −5 to −20° C., most preferably about −15° C.

The cathode reaction vessel (12) and the anode reaction vessel (14) may be pressurized to a pressure of from 5 to 1000 bar, typically from 5 to 500 bar, preferably from 5 to 200 bar, more preferably from 10 to 150 bar, more preferably from 20 to 150 bar, most preferably from 40 to 150 bar with a pressurizing fluid containing or comprising liquid carbon dioxide and hydrogen.

The cathode reaction vessel (12) may be pressurized with a mixture of hydrogen and carbon dioxide which may be present in a molar ratio of 4:1 to 1:4, from 2:1 to 1:4, from greater than 1:1 to 1:4 or even from 1:2 to 1:4.

Preferably, sufficient aqueous growth substrate is provided in the cathode reaction vessel (12) to provide an aqueous growth substrate to head space volumetric ratio of 1:1 to 4:1, typically a volumetric ratio of 2:1 to 3:1.

The pH of the aqueous growth medium is preferably maintained in the range from 6 to 7.5, preferably 6.5 to 7.

The voltage applied across the positive electrode and the negative electrode may be from −0.2 v to −40 v, −2 v to −40 v, −10 v to −40 v, −20 to −40 v, typically −25 v to −35 v.

The direct electrical current flowing across the positive electrode and the negative electrode may be approximately 75-125 mAmps.

According to a second embodiment of the invention, there is provided an apparatus for the production methane from carbon dioxide and water in the presence of hydrogen and methanogen/s comprising:

a cathode reaction vessel (12) for containing carbon dioxide and electrolytic water;

an anode reaction vessel (14) for containing electrolytic water;

a negative electrode (cathode) capable of supporting methanogens located within the cathode reaction vessel (12);

a positive electrode (anode) located within the anode reaction vessel (14); and connection means for connecting electrolytic water in the cathode reaction vessel (12) and anode reaction vessel (14) so that an electric current can flow between the two.

The cathode reaction vessel (12) and the anode reaction vessel (14) are preferably adapted to be pressurized to a pressure of from 5 to 1000 bar, typically from 5 to 500 bar, preferably from 5 to 200 bar, more preferably from 10 to 150 bar, more preferably from 20 to 150 bar, most preferably from 40 to 150 bar.

The connection means is preferably a conduit containing liquid electrolyte.

The conduit may include a semi-pervious membrane which allows the passage of ions between the electrolytic water in the anode reaction vessel (14) and cathode reaction vessel (12).

Preferably, the conduit has a valve which does not make electrical contact with the electrolyte.

The negative electrode in the cathode reaction vessel (12) is preferably in the form of a porous structure capable of supporting methanogens and biofilms they may generate. For example, the negative electrode in the second reaction vessel (12) is a hollow microporous cylinder which is closed at one end and which is made from a Pt amalgam or Pt, or Platinum Group Metal, or Titanium, or Platinum Group Metal plated Titanium.

The positive electrode in the anode reaction vessel (14) is preferably made of Pt or Platinum Group metal, or electroplated Titanium.

The internal surfaces of the reaction vessels may be made from non-conductive high temperature, high pressure withstanding materials, for example PEEK (polyether ether ketone), and insulate the electrolytic media from the rest of the apparatus, except for the cathode and anode which come in to contact with solution within the reaction vessels.

Preferably, the cathode reaction vessel is adapted to be pressurised with a pressurizing fluid.

Preferably, the apparatus includes means for equalizing the pressure in the cathode reaction vessel (12) and anode reaction vessel (14).

The pressure equalizing means is preferably pressurized by the pressurizing fluid used to pressurize the cathode reaction vessel (14) which also simultaneously pressurizes the anode reaction vessel (12).

Preferably, the pressurizing equalizing means provides electrical insulation between the cathode reaction vessel (12) and anode reaction vessel (14).

The pressure equalizing means may comprise a non-conductive high tensile high temperature resistant tube with a piston located therein, and an indicator for indicating the position of the piston within the tube.

Preferably, the apparatus includes heat control means for heating or cooling the cathode reaction vessel (12).

Preferably, a stirrer is provided within the cathode reaction vessel (12).

The conduit may be located in a non-conductive and heat-resistant barrier between the cathode reaction vessel (12) and anode reaction vessel (14).

DETAILED DESCRIPTION OF THE INVENTION

This invention relates to a method of producing methane from methanogen Archaea (methanogens) that are cultivated in an aqueous substrate solution, in the presence of carbon dioxide and hydrogen, at high pressure greater than or equal to 5 bar and up to 1000 bar using a pressurizing fluid containing or comprising carbon dioxide. The invention also relates to an apparatus for carrying out the methanogenesis reaction.

The methanogenesis reaction is maintained under anaerobic conditions.

Figure 1:
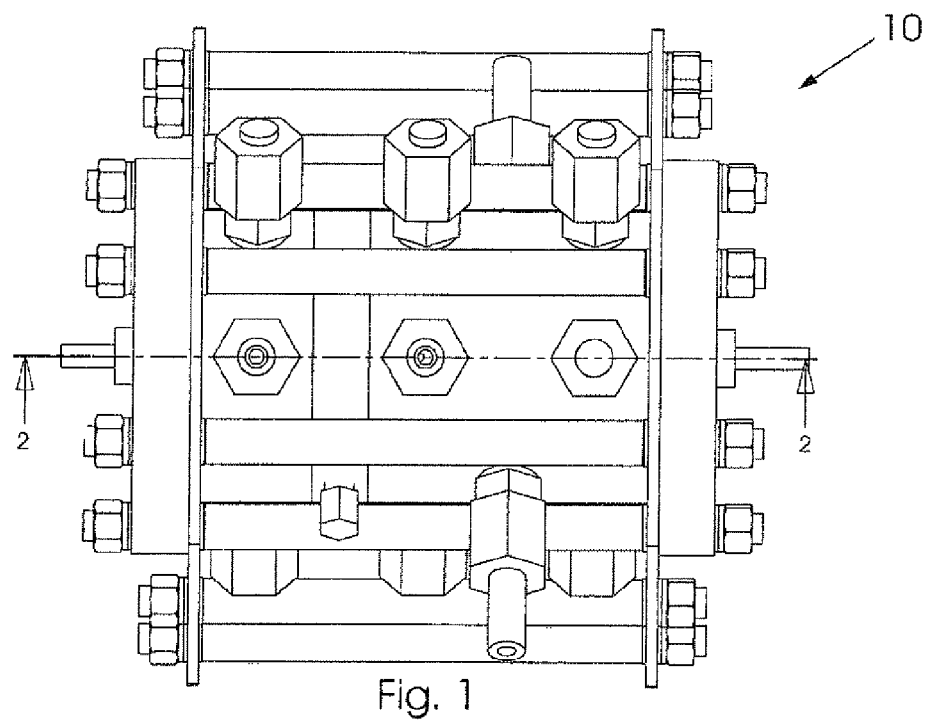
FIG. 1 is side view of a reactor according to an embodiment of the invention.
Figure 2:
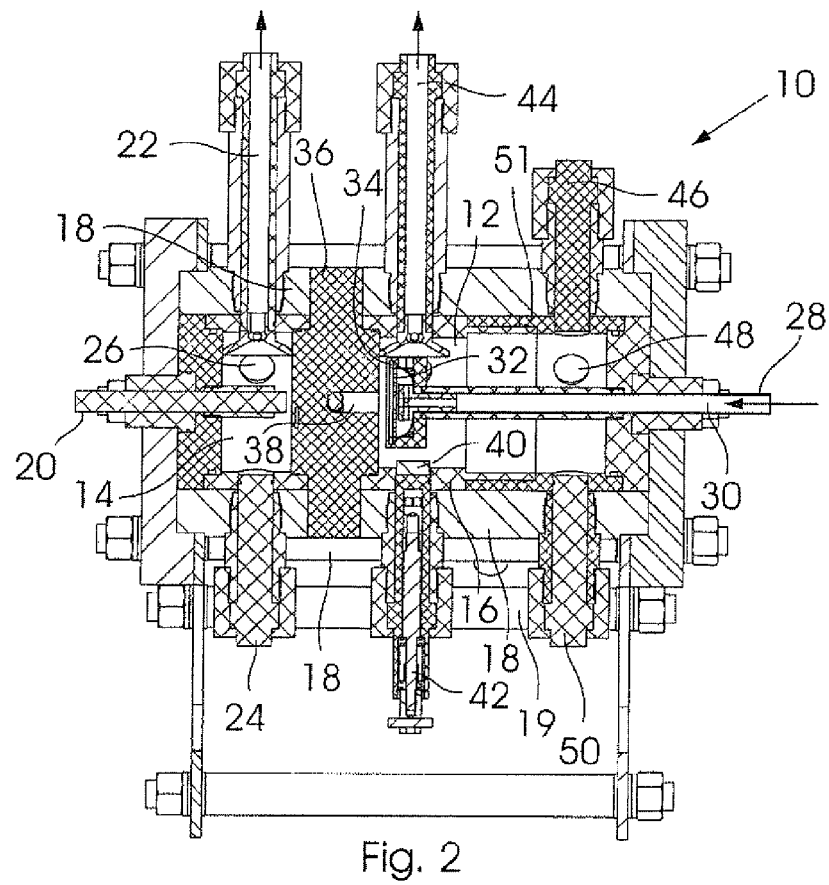
FIG. 2 is cross-sectional view of the reactor shown in FIG. 1, through the line 2-2.

With reference to FIGS. 1 and 2, methanogens are cultivated in a reactor indicated generally by the numeral 10. The reactor 10 comprises reaction chambers 12 and 14 which are adapted to operate at a temperature up to or greater than or equal to 500° C. and at an internal pressure of greater than or equal to 5 bar and up to 1000 bar.

The reaction chambers 12 and 14 are defined in tubes 16 made from a non-conductive material able to withstand high temperatures (in this case polyether ether ketone (PEEK)), which is reinforced within a metal casing 18 held together by metal tie-bars 19.

Extending into the "anode" reaction chamber 14 is a positive electrode (anode) 20 made from sintered platinum or rhodium plated titanium. An outlet 22 is provided for removing material from the anode reaction chamber 14, and inlets 24 and 26 are provided for supplying material into the anode reaction chamber 14.

Extending into the "cathode" reaction chamber 12 is a negative electrode (cathode) 28 made from sintered platinum or rhodium plated titanium, or titanium. The negative electrode 28 has a hollow core 30, with a perforated disc 32 which is covered with a carbon cloth 34 that is capable of supporting methanogens and which is conducive to methanogens forming biofilms.

An insulating barrier 36, made from a non-conductive material, preferably PEEK, separates the reaction chambers 12 and 14, which are joined via a conduit 38 which extends through the barrier 36. The conduit 38 includes a valve mechanism which is used to open and close the conduit 38. The valve is insulated from the contents of the reaction chambers 12 and 14 and comprises a threaded sectioned smooth rod which when screwed inwards enables the smooth rod section to pass through a 'dog-leg' in the conduit to effectively obstruct the electrolyte continuity when fully screwed in. A membrane is secured within a cavity receptacle within the conduit 38. The cavity receptacle is located within the conduit 38 on the anode side of the valve separating the two vessels 12 and 14 to house a pair of short sockets/bushes to secure the thin membrane between them. The sockets/bushes are located and fixed in position within the receptacle by a non-conductive circlip.

The distance between the electrodes 20 and 28 is preferably 60 mm or less. The internal surfaces of the reaction chambers 12 and 14, including the valve electrolyte contacting surfaces, insulate electrolytic media within these chambers from the rest of the apparatus, except for the electrodes 20 and 28 which come in to contact with electrolytic media within the chambers 12 and 14.

Located within the cathode reaction chamber 12 below the carbon cloth 34 is a non-conductively coated magnetic stirrer bar 40 which is actuated by a rotatable magnetic stirrer mechanism 42.

An outlet 44 is provided for removing material from the cathode reaction chamber 12, and inlets 46, 48 and 50 are provided for supplying material into the cathode reaction chamber 12.

The outlets may have electrically, pneumatically or hydraulically activated solenoid valves (not shown in the drawings) connecting the reactors with the outlet connection means to outer collection or supply vessels.

The electrodes 20 and 28 are connected together and supplied with power by a DC power supply.

Figure 3:
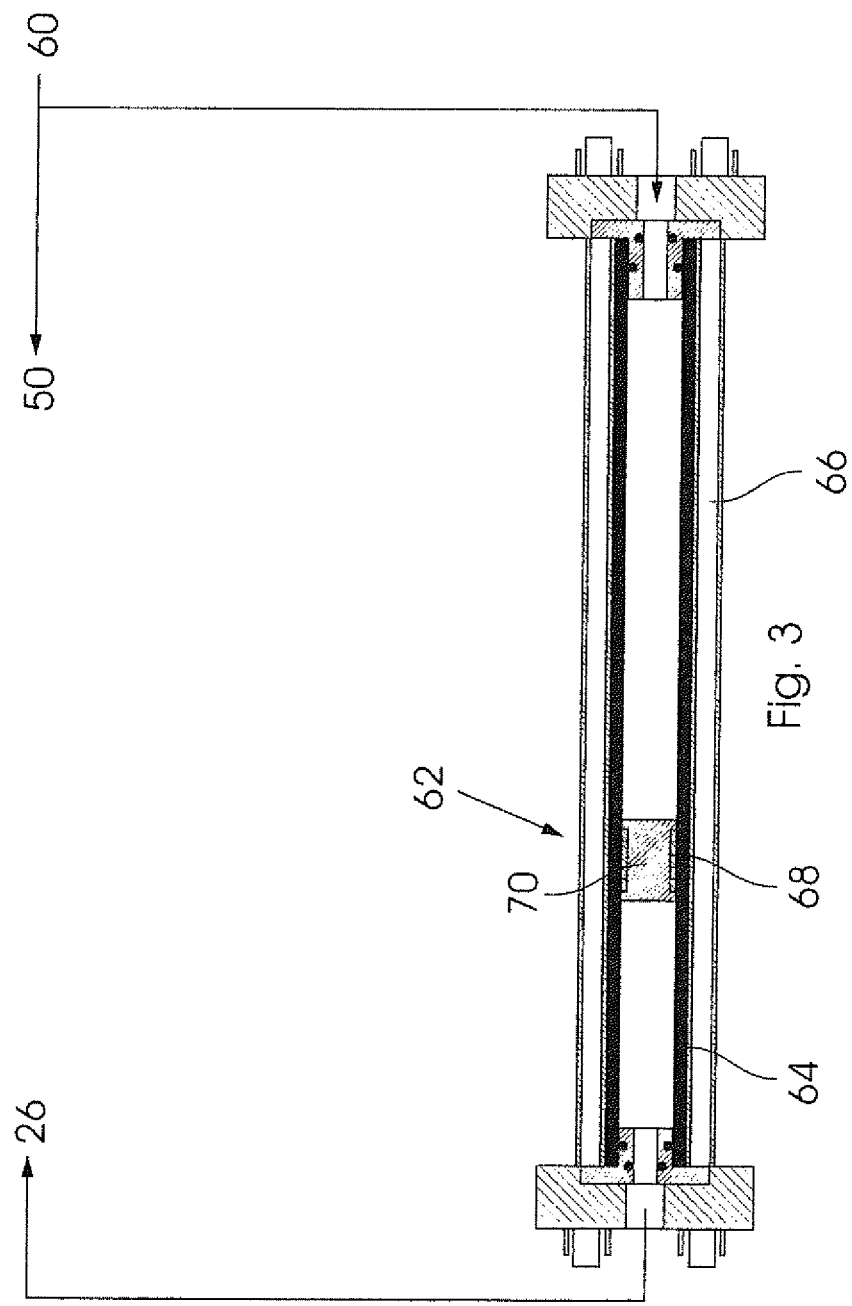
FIG. 3 is a cross-sectional view of an apparatus for equalizing the pressure within the reactor vessels on the reactor according to an embodiment of the invention.

Means is provided to control the pressure within the anode reaction vessel 14 and to equalize its internal pressure with the pressure within cathode reaction vessel 12: with reference to FIG. 3, pressurized $CO_2$ and/or $H_2/CO_2$ mixture 60 is supplied directly to the inlet 50 of the cathode reaction vessel. The pressurized $CO_2$ and/or $H_2/CO_2$ is connected to the anode reaction vessel via a high pressure equaliser 62 which prevents the $CO_2$ and/or $CO_2/H_2$ mixture from contacting or reacting with the contents of anode reaction vessel 14. The high pressure equaliser 62 comprises a pipe 64 made from a non-conductive high tensile high temperature resistant tubing and is covered by a housing 66 which is capable of withstanding high pressures at and above 5 bar and up to 1000 bar. Located within the pipe 64 is a piston 68. The piston 68 can move along the length of the pipe 66 and seals the $CO_2$ and/or $H_2/CO_2$ on the cathode side of the pipe 66 from electrolyte on the anode side of the pipe 64 while equally transmitting the pressure to the anode contents. An indicator is provided to indicate the position of the piston 68 within the pipe 64—in this case the indicator is a magnetic metal ball 70 located within the piston 68 which activates light-emitting diodes (LEDs—not shown) placed along the length of the pipe 64. The LEDs light up when they come in to contact with the magnetic field of the magnetic ball 70, and thus indicate the position of the piston 68 within the pipe 64.

In use, before startup of the electrolytic process, the valve in the conduit 38 is closed and anode electrolyte is transferred in to the anode reaction vessel 14 through the inlet 26. The anode electrolyte comprises an aqueous solution containing 1.25M $Mg_2SO_4$.

An aqueous methanogens substrate solution is transferred in to the cathode reaction vessel 12 through the inlet 48. The aqueous substrate solution comprises a combination of minerals (mainly chloride, sulphate and carbonate salts as well as Wolfe's minerals, and methanogens vitamins such as Wolf's vitamins that are able to support methanogens. The solution has a pH in the range from 6 to 7.5, preferably 6.5 to 7. The solution is inoculated with methanogen/s cells under anaerobic conditions and then transferred in to the cathode reaction vessel via an inlet 46. Sufficient aqueous methanogens substrate solution is transferred into the cathode reaction vessel 12 to leave an anaerobic headspace. The ratio between the volume of the headspace and the volume of the solution is typically from 1:1 to 1:3.

The inlet 26 of the anode reaction vessel 14 is connected to the pressure equaliser 62. $CO_2$ is pumped in to the cathode reaction vessel 12 via the inlet 48 to purge the headspace of air including oxygen, which exits through the outlet 44. The inlets 24, 48 and 46 and also the outlets 22 and 44 are closed and the cathode reaction vessel 12 is pressurized with liquid $CO_2$. When the pressure within the reaction vessels 12 and 14 is the same, the valve in the conduit 38 is opened and equal pressure is maintained within the reaction vessels 12 and 14 by making use of the high pressure equaliser 62. The pressure in the reaction vessels 12 and 14 may be maintained at 5 bar to 1000 bar. It has been found that increased pressure of $CO_2$ can lead to the lowering of the pH of the aqueous methanogens substrate solution. This is problematic when the pH reaches 5.5 and lower. Ideally the pH needs to be maintained in the range from 6 to 7.5, preferably 6.5 to 7.

The temperatures within the reaction vessels 12 and 14 may be the same, or they may be heated or cooled separately by heating or cooling recycled materials to the vessels. The temperature within the reaction vessel 12 may be controlled by heating an insulated copper or heat-conductive material 51 by means of a heating cartridge or element(s) near to it.

The methanogen/s may be anaerobic Archaea, which may be a hyperthermophilic, hyperextremophile or, psychrophile/cryophile and/or an exoelectrogenic microbiological organism.

Examples of methanogens include *Methanobacterium Methanobacterium bryantii, Methanobacterium congolense, Methanobacterium defluvii, Methanobacterium espanolae, Methano-bacterium formicicum, Methanobacterium ivanovii, Methanobacterium palustre, Methanobacterium thermaggregans, Methanobacterium uliginosum, Methanobrevibacter acididurans, Methanobrevibacter arbor iphilicus, Methanobrevibacter gottschalkii, Methanobrevibacter olleyae, Methanobrevibacter ruminantium, Methanobrevibacter smithii, Methanobrevibacter woesei, Methanobrevibacter wolinii, Methanothermobacter marburgensis, Methanothermobacter thermo-autotrophicus, Methanobacterium thermoautotrophicus, Methanothermobacter thermoflexus, Methanothermobacter thermophilics, Methanothermobacter wolfeii, Methanothermus sociabilis, Methanocorpusculum bavaricum, Methanocorpusculum parvum, Methanoculleus chikuoensis, Methanoculleus submarinus, Methanogenium frigidum, Methanogenium liminatans, Methanogenium marinum, Methanosarcina acetivorans, Methanosarcina barker, Methanosarcina mazei, Methanosarcina thermophila, Methanomicrobium mobile, Methanocaldococcus jannaschii, Methanococcus aeolicus, Methanococcus maripaludis, Methanococcus vannielii, Methanococcus voltaei, Methanothermococcus thermolithotrophicus*.

In the case where the methanogen/s is/are a hyperthermophilic hyperextremophile anaerobic Archaea, the cathode reaction vessel (12) may be operated at a temperature of 50° C. to 400° C., preferably 80° C. to 200° C., more preferably 80° C. to 150° C. In the case where the methanogen/s is/are a psychrophile/cryophile anaerobic Archaea, the cathode reaction vessel (12) may be operated at a temperature of −50 to 50° C., preferably −5 to −20° C., most preferably about −15° C.

In addition to $CO_2$, $H_2$ may be supplied to the cathode reaction chamber 12 via the inlet 50 respectively, so that the cathode reaction chamber is pressurized with a mixture of $CO_2/H_2$. The $H_2$ and $CO_2$ may be added in a molar ratio of 4:1 to 1:4, from 2:1 to 1:4, from 1:1 to 1:4 or even from 1:2 to 1:4. The concentrations of $CO_2$ and $H_2$ are maximised by excluding other materials for pressurization so that the maximum reactor system volume may utilized for conversion to $CH_4$.

In accordance with the present invention, typical methanogens are thermophilic methanogenic archaea, for example:

of the class Methanococci, namely *Methanocaldococcus jannaschii* (formerly *Methanococcus jannaschii*) preferred temperature is 85° C., of the genus *Methanopyrus*, namely *Methanopyrus kandleri*—preferred temperature is 105° C., and of the genus *Methanothermococcus*, namely *Methanothermococcus thermolithotrophicus* preferred temperature is 65° C.

An electrolysis reaction is initiated by applying a direct voltage of −0.2 up to −35 v, typically −20 to −35 v, across the positive electrode 20 and negative electrode 28. The direct electrical current flowing across the positive electrode and the negative electrode may be approximately 75-125 mAmps, typically about 100 mAmps. The applied charge ionizes atoms in the electrolytic media in the reaction vessels. The initiation of the electrolysis process causes nascent (ionized) hydrogen ions to be formed from the $H_2O$ present in the electrolytic medium. In accordance with the present invention, the electrolysis reaction not only produces hydrogen, but also increases the pH of the aqueous substrate solution and can be used to control the pH of the solution to a pH above 5.5 at which methanogens can not only produce methane but can also grow (i.e. reproduce), in the range from 6 to 7.5, preferably 6.5 to 7. According to a method according to the present invention, the pH of the aqueous substrate solution is initially provided in the correct range from 6 to 7.5 by the electrolytes in the medium. Pressurising with $CO_2$ increases the acidity and thus the pH decreases. Should the pH fall too low, electrolysis is implemented intermittently to increase alkalinity and drive the pH up into the required range.

Reaction product, including hydrocarbons may be retrieved from the outlet 44. In the anode reaction vessel 14, the electron flow causes oxygen ions which are negatively charged to be attracted to the positively charged electrode 20 therewithin, thus liberating the oxygen molecules at the electrode. Oxygen product may be retrieved from the outlet 22.

The conduit 38, which may have unidirectional-flow cation properties, is necessary to allow the transfer of electrons and keep the liberated oxygen in the reaction vessel 14 away from the reaction vessel 12 to avoid recombination with carbon and/or hydrogen there and oxygen contamination of the anaerobic Archaea. The barrier 36 also serves to reduce heat conduction transfer so that different temperature conditions may be maintained in the reaction vessels 12 and 14 to enhance and facilitate the different reactions occurring therein and save energy costs.

If necessary, methanogens may be supplied into the reaction chamber 12 through the hollow core 30 of the electrode 28, and these settle on the carbon cloth 34 which provides a haven for the methanogens to develop biofilms and to perform methanogenesis.

The charge polarization serves to separate the oxygen and methane produced from one another for sufficient short period for the methanogens to do their conversion work and also to enhance the process by enhanced electrolysis. During this process the oxygen is produced at the anode 20, away from the negatively charged cathode 28 where the methanogenesis reaction occurs providing sufficiently anaerobic conditions in the cathode vicinity while the current is flowing through the circuit.

The outgoing stream may be recycled after separation of the methane produced from unreacted materials, removal of the dead or inactive methanogens is achieved, and the process may be repeated continuously.

In accordance with a further aspect of the invention, it has been found that the methanogenesis reaction can be improved at higher pressures by adding hydrogen to the headspace of the cathode reaction vessel 14.

In accordance with an embodiment of the invention, a standard procedure was developed, and the standard conditions were:

Cathode: 100 ml head-space, 300 ml medium; Inoculum with 0.5 g frozen cells.

Anode: completely full with 1.25 M $MgSO_4$-solution (~100 ml) Voltage: 30 V

Procedure: Inoculation at room temperature, electrolysis starts automatically during the night. The first headspace measurement is on the next day in the morning. If the hydrogen content is >50 vol. %, electrolysis is stopped. Then heating to appropriate temperature is started. Several headspace measurements are following (~3 h of incubation, 6 h of incubation, the next day in the morning) until the produced hydrogen has (completely) been converted into methane.

Experiments were conducted using the apparatus illustrated in FIGS. 1-3 and described above using three strains of hyperthermophilic methanogens: *Methanocaldococcus jannaschii* (formerly *Methanococcus jannaschii*), *Methanopyrus kandleri*—preferred temperature is 105° C., and *Methanothermococcus Methanothermococcus thermolithotrophicus*. All three strains have been tested according to this procedure.

The following experiments were conducted:
1. *Mc. thermolithotrophicus*, 10 bar, 30 V, 65° C., 300 ml electrolyte/100 ml headspace
2. *Mc. thermolithotrophicus*, 20 bar, 30 V, 65° C., 300 ml electrolyte/100 ml headspace
3. *M. kandleri*, 10 bar, 30 V, 97° C., 300 ml electrolyte/100 ml headspace
4. *M. kandleri*, 20 bar, 30 V, 97° C., 300 ml electrolyte/100 ml headspace
5. *M. kandleri*, 20 bar, 30 V, 105° C., 300 ml electrolyte/100 ml headspace
6. *Mc. jannaschii* 10 bar, 30 V, 85° C., 300 ml electrolyte/100 ml headspace
7. *Mc. jannaschii* 10 bar, 30 V, 92° C., 300 ml electrolyte/100 ml headspace
8. *Mc. jannaschii* 20 bar, 30 V, 92° C., 300 ml electrolyte/100 ml headspace A summary of the test results is provided in the Table 1 below:

The conversation rate of $H_2$ to $CH_4$ was 98.2%

The $CH_4$ production rate was 12.1 ml/h

With reference to Example 14—experiment with *Methanocaldococcus jannaschii* at 30 V and 92° C. and 20 bar:

65.5 vol. % $H_2$ was produced from electrolysis (initial headspace)

The methanogens converted the hydrogen completely to 31 vol. % $CH_4$ at a constant temperature of 92° C. The final volume percentage of $H_2$ in the headspace was 0.4 vol. %

The conversation rate of $H_2$ to $CH_4$ was 99.4%

The $CH_4$ production rate was 21.1 ml/h

These two experiments are comparable because the temperature, the electrolyte, the ratio of headspace to medium, the procedure of inoculation and the voltage remained constant. No external hydrogen had been added.

These two experiments support the following conclusions:
1. That increased pressure increases the efficiency and the biological production rate of $CH_4$ from $H_2$ (produced from $H_2O$ electrolysis) and $CO_2$. The conversation rate in the 20 bar experiment was higher than in the 10 bar experiment.
2. The methanogens used up all the produced hydrogen from the production of methane due to methanogenesis.
3. Biological production of methane (methanogenesis) using the method of this invention does not necessarily require a

TABLE 1

| ORGANISM TEMPERATURE [° C.] | EXAMPLE | DURATION [H] | PERCENTAGE COMPOSITION OF METHANE IN THE HEAD SPACE | CH4 PRODUCED IN TOTAL [ML] | CH4 PRODUCED PER ML OF CULTURE [ML/ML] | CH4 PRODUCTION RATE [ML/H]* |
|---|---|---|---|---|---|---|
| 1. 10 bar *Mc. thermo-lithotrophicus* CO2 and 30 V 65 | Example 6 | 45.75 in total 29 with heating | 18 | 184 | 0.6 | 4/6.3 |
| 2. 20 bar *Mc. thermo-lithotrophicus* CO2 and 30 V 65 | Example 7 | 69 in total 51.5 with heating | 22.5 | 399 | 1.3 | 5.8/7.7 |
| 3. 10 bar *M. kandleri* CO2 and 97 30 V | Example 9 | 41 in total 24 with heating | 15 | 120 | 0.4 | 5 |
| 4. 20 bar *M. kandleri* CO2 and 97 30 V | Example 10 | 47 in total 40.5 with heating | 25 | 400 | 1.3 | 9.9 |
| 5. 20 bar *M. kandleri* CO2 and 105 30 V | Example 11 | 48.5 in total and 29.5 with heating | 19 | 285 | 0.95 | 9.7 |
| 6. 10 bar *Mc. jannaschii* CO2 and 85 30 V | Example 12 | 41 in total and 22.5 with heating | 30.5 | 244 | 0.8 | 10.8 |
| 7. 10 bar *Mc. jannaschii* CO2 and 92 30 V | Example 13 | 41.5 in total and 16 with heating | 19.5 | 195 | 0.65 | 12.2 |
| 8. 20 bar *Mc. jannaschii* CO2 and 92 30 V | Example 14 | 41.5 in total and 22 with heating | 31 | 465 | 1.55 | 21.1 |

The results reflected Table 1 indicate that the methane production rate and total vol. % of methane increase with increasing pressures and test temperatures. Incubation temperature for the respective organism should be around its temperature optimum.

With reference to Example 13—experiment with *Methanocaldococcus jannaschii* at 30 V. 92° C. and 10 bar:

About 57 vol. % $H_2$ was produced from electrolysis at 30 V (initial headspace) The methanogens converted the hydrogen completely to 19 vol. % CH at a constant temperature of 92° C. The final volume percentage of $H_2$ in the headspace was 1 vol. %

4:1 $H_2:CO_2$ ratio. When $CO_2$ is in the excess the complete consumption of hydrogen may be favoured (compared to a 4:1 ratio hydrogen:$CO_2$).

1 atm=101,325 kPa
1 bar=100 kPa

The Invention will now be described in more detail with reference to the following non-limiting Examples.

Example 1

In the examples, three methanogens *M. kandleri*, *M. thermolithotrophicus* and *M. jannaschii* were tested for the production of methane.

The following growth aqueous substrate solutions (growth media) were used in the Examples:

MJ Medium—for *M. jannaschii*

| Additive | Amount |
|---|---|
| NaCl | 30.0 g |
| NaHCO$_3$ | 1.00 g |
| MgCl$_2$ × 6H$_2$O | 4.10 g |
| MgSO$_4$ × 7H$_2$O | 3.40 g |
| KCl | 0.33 g |
| NH$_4$Cl | 0.25 g |
| K$_2$HPO$_4$ | 0.14 g |
| CaCl$_2$ × 2H$_2$O | 0.14 g |
| (NH$_4$)$_2$Fe(SO$_4$)$_2$ × 6H$_2$O | 0.01 g |
| NiCl$_2$ × 6H$_2$O | 0.5 mg |
| NaSeO$_4$ | 0.5 mg |
| Wolfe's Minerais 10x/pH 1.0/neu-T | 1.0 ml |
| Wolfe's Vitamins 10x | 1.0 ml |
| Resazurin, 0.1% ig | 1.0 ml |
| Na$_2$S × 7-9 H$_2$O | 0.5 g |
| alternativ: | |
| Na$_2$S × 2H$_2$O | 0.25 g |
| H$_2$O, ad | 1000.0 ml |

| Wolfe's minerals | | |
|---|---|---|
| Additive | Amount | Concentration |
| MgSO$_4$ × 7H$_2$O | 30.0 g | 121.70 mM |
| MnSO$_4$ × H$_2$O | 5.00 g | 29.60 mM |
| NaCl | 10.0 g | 171.10 mM |
| FeSO$_4$ × 7H$_2$O | 1.00 g | 3.60 mM |
| CoCl$_2$ × 6H$_2$O | 1.00 g | 7.57 mM |
| CaCl$_2$ × 2H$_2$O | 1.00 g | 6.80 mM |
| ZnSO$_4$ × 7H$_2$O | 1.80 g | 6.30 mM |
| CuSO$_4$ × 5H$_2$O | 0.10 g | 0.40 mM |
| KAl(SO$_4$)$_2$ × 12H$_2$O | 0.18 g | 0.38 mM |
| H$_3$BO$_3$ | 0.10 g | 1.62 mm |
| Na$_2$MoO$_2$ × 2H$_2$O | 0.10 g | 0.41 mM |
| (NH$_4$)$_2$Ni(SO$_4$)$_2$ × 6H$_2$O | 2.80 g | 7.09 mM |
| Na$_2$WO$_4$ × 2H$_2$O | 0.10 g | 0.30 mM |
| Na$_2$SeO$_4$ | 0.10 g | 0.53 mM |
| H$_2$O, ad | 1000.0 ml | |

| Wolfe's vitamins | | |
|---|---|---|
| Additive | Amount | Concentration |
| Biotin | 20 mg | 81.9 μM |
| Folsaure | 20 mg | 45.3 μM |
| Pyridoxamindihydrochlorid = Vit. B6 | 100 mg | 386.0 μM |
| Thiamindihydrochlorid = Vit. B1 | 50 mg | 148.0 μM |
| Riboflavin = Vit. B2 | 50 mg | 133.0 μM |
| Nikotinsaure | 50 mg | 406.0 μM |
| DL-Calciumpantothenat | 50 mg | 105.0 μM |
| Cyanocobalamin = Vit. B12 | 1 mg | 0.74 μM |
| p-Aminobenzoesaure = PABA | 50 mg | 365.0 μM |
| Liponsaure | 50 mg | 242.0 μM |
| H$_2$O bidest, ad | 1000 ml | |

SME Medium (synthetic sea water)—for *M. kandleri*

| Additive | Amount |
|---|---|
| SME stock-solution | 1000.0 ml |
| KH$_2$PO$_4$ | 0.5 g |
| NH$_4$Cl | 0.5 g |
| Wolfe's Minerals/10x/pH 1.0/neu-T | 1.0 ml |
| Resazurin, 0.1% ig | 1.0 ml |
| Na$_2$S × 7-9H$_2$O | 0.5 g |
| alternativ: | |
| Na$_2$S × 2H$_2$O | 0.25 g |

| SME stock-solution | | |
|---|---|---|
| Additive | Amount | Concentration |
| NaCl | 27.7 g | 473.99 mM |
| MgSO$_4$ × 7H$_2$O | 7.0 g | 28.4 mM |
| MgCl$_2$ × 6H$_2$O | 5.5 g | 27.1 mM |
| CaCl$_2$ × 2H$_2$O | 0.75 g | 5.1 mM |
| KCl | 0.65 g | 8.7 mM |
| NaBr | 0.1 g | 0.97 mM |
| H$_3$BO$_3$ | 0.03 g | 0.49 mM |
| SrCl$_2$ × 6H$_2$O | 0.015 g | 0.056 mM |
| KJ-Lsg., 0.1% ig | 0.1 ml | 0.30 μM |
| H$_2$O, ad | 1000.0 ml | |

MGG medium—for *M. thermolithotrophicus*

| Additive | Amount |
|---|---|
| NaCl | 18.00 g |
| NaHCO$_3$ | 5.50 g |
| MgSO$_4$ × 7H$_2$O | 3.40 g |
| MgCl$_2$ × 6H$_2$O | 4.30 g |
| KCl | 0.35 g |
| K$_2$HPO$_4$ × 3H$_2$O | 0.14 g |
| NH$_4$Cl | 0.25 g |
| CaCl$_2$ × 2 H$_2$O | 0.14 g |
| (NH$_4$)$_2$ Fe(SO$_4$)$_2$ × 6H$_2$O | 0.002 g |
| Wolfe's Minerals 10x/pH 1.0/neu-T | 1.0 ml |
| Resazurin, 0.1% ig | 1.0 ml |
| Na$_2$S × 7-9H$_2$O | 0.5 g |
| alternativ: | |
| Na$_2$S × 2 H$_2$O | 0.25 g |
| H$_2$O, ad | 1000.0 ml |

Example 2

CO$_2$-Experiment at 50 Bar without Electrolysis

This experiment was performed to determine the influence of CO$_2$ on the pH value of the electrolyte.

The test was started at 65° C. with 50 bar CO$_2$. The electrolyte in the cathode chamber was SME, pH 7. The change of pH was monitored every 15 minutes. The results of the Experiments are shown in Table 2 below.

TABLE 2

| DATE | TIME | PRESSURE | TEMPERATURE | pH AT THE CATHODE |
|---|---|---|---|---|
| May 12, 2012 | 11.00 | atmospheric | 65° C. | 7 |
| May 12, 2012 | 13.50 | 50 bar CO$_2$ | 65° C. | 7 |
| May 12, 2012 | 14.05 | 50 bar CO$_2$ | 65° C. | 6.5 |
| May 12, 2012 | 14.20 | 50 bar CO$_2$ | 65° C. | 5.5 |
| May 12, 2012 | 14.35 | 50 bar CO$_2$ | 65° C. | 5.5 |
| May 12, 2012 | 14.50 | 50 bar CO$_2$ | 65° C. | 5.5 |
| May 12, 2012 | 14.02 | 80 bar CO$_2$ | 65° C. | pressurized up to 80 bar |
| May 12, 2012 | 14.17 | 80 bar CO$_2$ | 65° C. | 5.5 |

Figure 4:
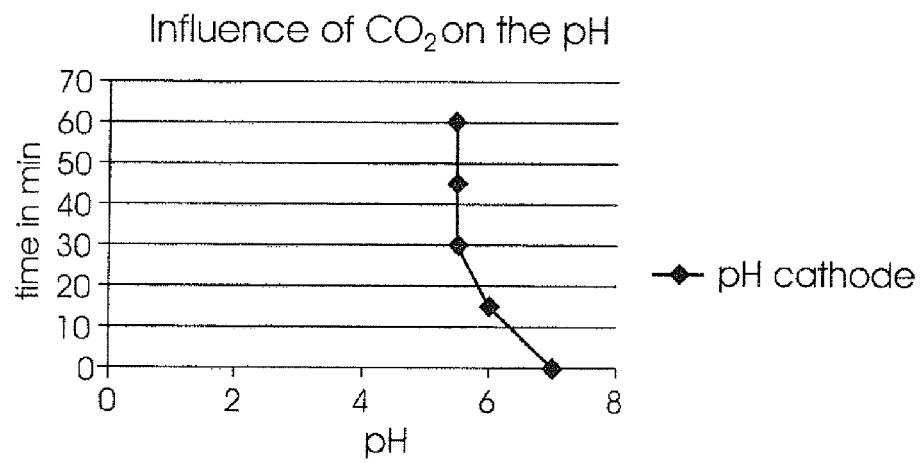
FIG. 4 is a graph showing the results of an experiment to determine the influence of $CO_2$ on the pH of electrolytic aqueous growth substrate.

The influence of CO$_2$ on the pH is shown in FIG. 4.

Conclusion: At a pressure of 50 bar CO$_2$ the pH dropped from 7 to 5.5 and stayed constant at this value. A pH of 5.5 is the minimum pH the methanogens can tolerate.

Example 2

Electrolysis Experiment at 65° C. and Atmospheric Pressure (No $CO_2$ Present)

This experiment was conducted to determine the effect of the electrolysis reaction on pH when no $CO_2$ is present.

Figure 5:
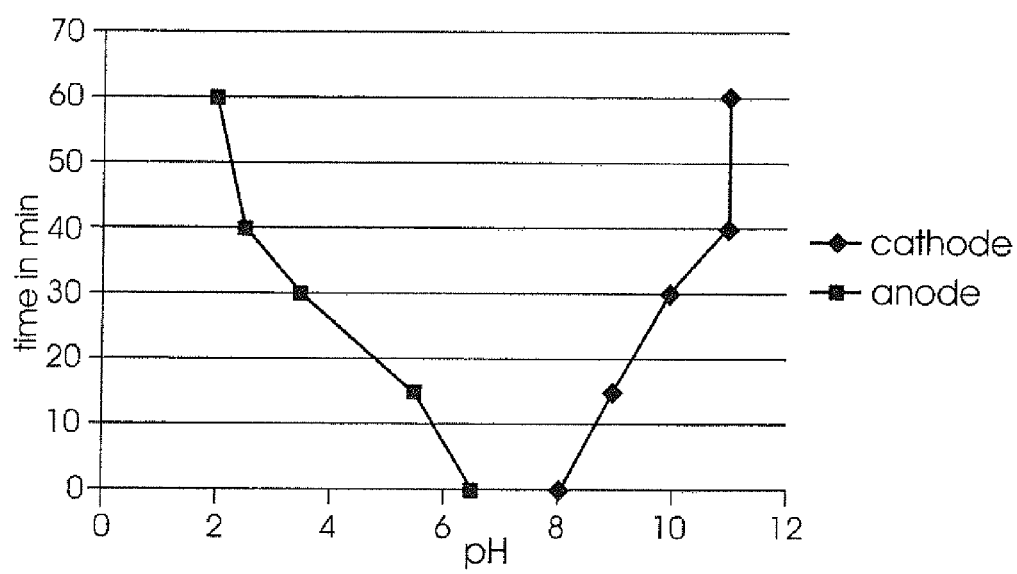
FIG. 5 is a graph showing the results of an experiment to determine the effect of electrolysis on the pH of electrolytic media used in the present invention.

Electrolyte: SME (cathode), SME without chlorides (anode)
Voltage: 31.5 V constant
Gas phase: air
The results of the Experiments are shown Table 3 and FIG. 5.

|  | AT THE BEGINNING (AT 65° C.) | AFTER 15 MIN | AFTER 30 MIN | AFTER 45 MIN | AFTER 1 H | AFTER 2 H |
|---|---|---|---|---|---|---|
| Current | 220 mA | 250 mA | 320 mA | 300 mA | 320 mA | 300 mA |
| pH anode | 6.5 | 5.5 | 3.5 | 2.5 | 2 | 2 |
| pH cathode | 8 | 9 | 10 | 11 | 11 | 11 |

The pH at the cathode increased from 8 to 11 and stayed constant at 11. The pH at the anode became acidic and dropped from 6.5 to 2.

Conclusion: Due to electrolysis the electrolyte in the cathode became alkaline and the anode reaction room became acidic. A pH of 11 at the cathode is far too high for the methanogens. Their pH range is form 5.5 to 8 with an optimum around 7. The electrolysis reaction can be used to control the pH of the solution.

Example 4

Figure 6:
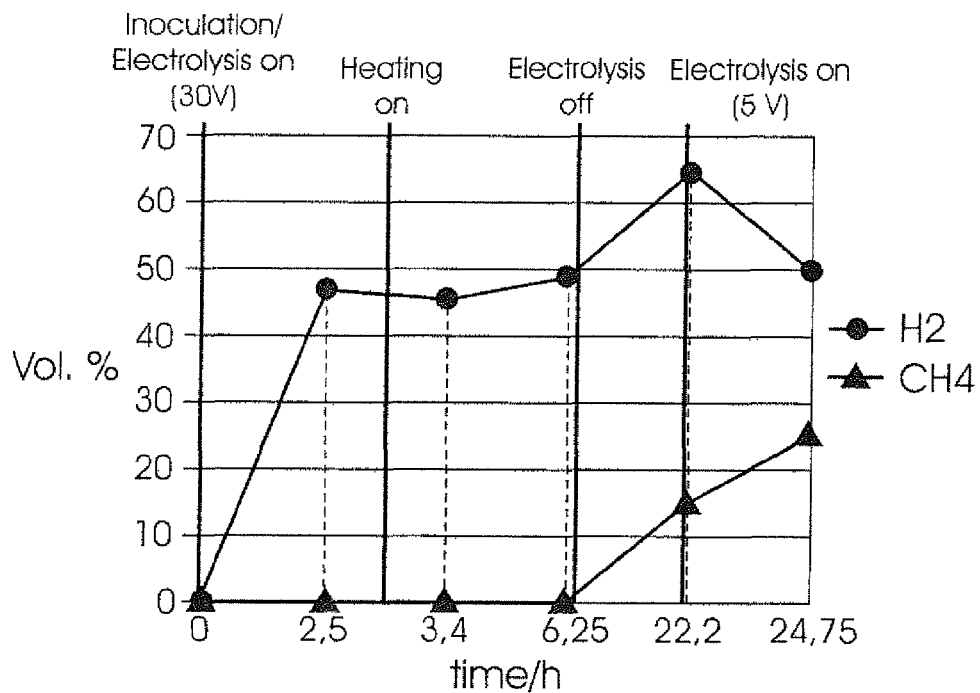
FIG. 6 is a graph showing the results of an experiment with *Mc. thermolithotrophicus*, 5 bar, 30 V, 65° C.

FFGF-reaction with *Mc. thermolithotrophicus* at 5 bar $CO_2$ and 30 V
Electrolyte cathode: 280 ml SME, pH 6.5
Electrolyte anode: $Mg_2SO_4$, 1.25 M
inoculum: 0.8 g frozen cells and 20 ml liquid pre-culture
Gas-phase 5 bar $CO_2$
Start electrolysis immediately after inoculation; when enough hydrogen is present, heat up to final temperature.
Voltage 30 V
The results of this experiment are shown in FIG. 6.

In this experiment there was only $CO_2$ in the head-phase and no additional hydrogen. Hydrogen was produced only from electrolysis which was started immediately after inoculation. At a concentration of 45% hydrogen heating was switched on in order to activate the methanogens. Electrolysis ran for another ~3.5 h until stopped. During night the methanogens produced ~15% of methane from $CO_2$ and hydrogen. The last measurement showed that the head-space contains ~25% methane. After the experiment it was noticed, that the frozen cells were lying on top of the cathode and did not re-suspend into the medium. Therefore, liquid pre-cultures in the following experiments.

Example 5

Figure 7:
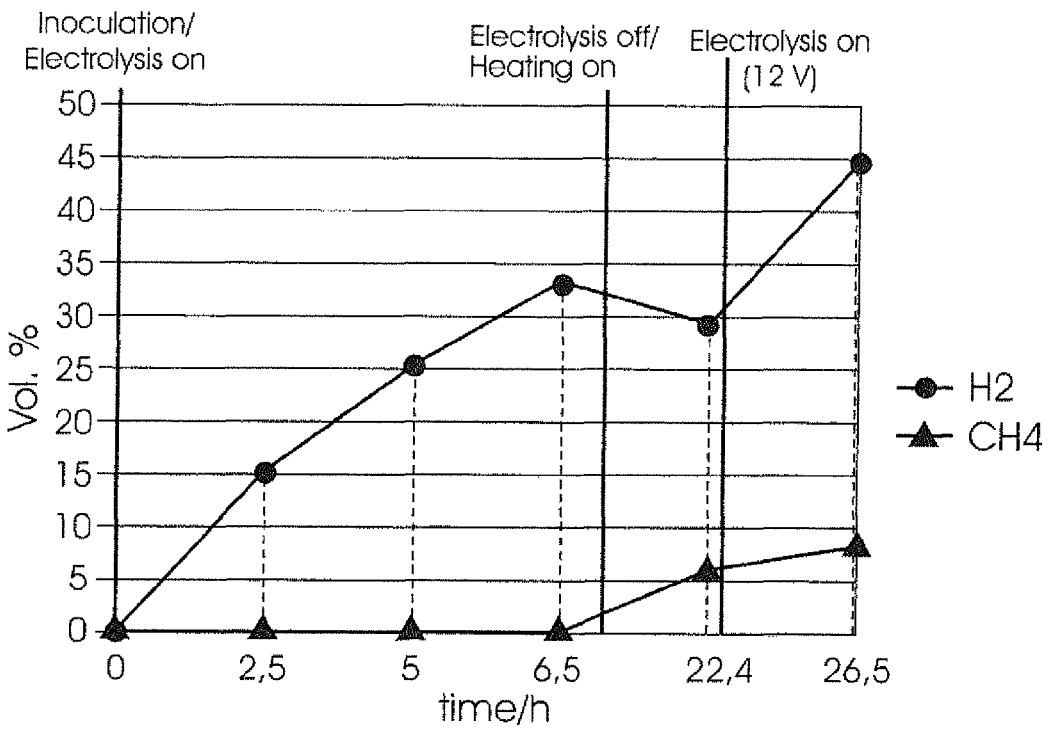
FIG. 7 is a graph showing the results of an experiment with *Mc. thermolithotrophicus*, 5 bar, 12 V, 65° C.

FFGF-reaction with *Mc. thermolithotrophicus* at 5 bar $CO_2$ and 12 V
Electrolyte cathode: 240 ml SME, pH 6.5
Electrolyte anode: $Mg_2SO_4$, 1.25 M
Inoculum: 60 ml liquid pre-culture
Gas-phase 5 bar $CO_2$
Start electrolysis immediately after inoculation; when enough hydrogen is present, heat up to final temperature
Voltage 12 V
5 ml gas-sample discarded, 10 ml gas-sample analyzed
The results of this experiment are shown in FIG. 7.

Under the same conditions as Example 4 but with electrolysis at 12 V it took longer to produce similar amounts of hydrogen from electrolysis (8 h and >33% $H_2$ vs. 2.5 h and 45% $H_2$). Electrolysis was stopped during the night. In the morning the methanogens had converted the hydrogen and $CO_2$ to ~6% methane. Electrolysis was restarted to investigate if more methane is produced and that was the case: A final concentration of ~8% $CH_4$ was reached. The yield is three times less when compared to the 5 bar experiment described in Example 4 with 30 V. It was concluded that more methane can be produced with higher voltage.

Example 6

Figure 8:
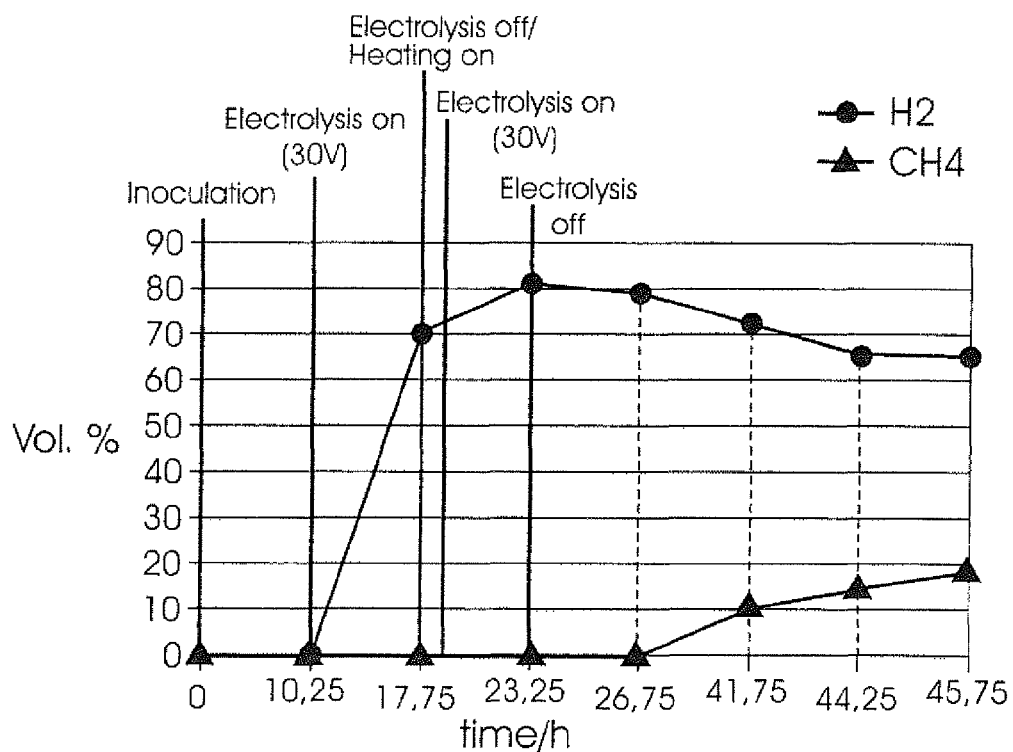
FIG. 8 is a graph showing the results of an experiment with *Mc. thermolithotrophicus*, 10 bar, 30 V, 65° C.

FFGF-reaction with *Mc. thermolithotrophicus* at 10 bar $CO_2$ and 30 V
Electrolyte cathode: 240 ml SME, pH 7
Electrolyte anode: $Mg_2SO_4$, 1.25 M
Inoculum: 60 ml liquid pre-culture
Gas-phase 10 bar $CO_2$
Voltage 30 V
The results of this experiment are provided in FIG. 8.

This experiment was performed at 10 bar $CO_2$ with no additional hydrogen. Hydrogen was produced from electrolysis at 30 V which has been started automatically at midnight. At this stage the reactor was at room temperature. In the morning when electrolysis ran for 8.5 h~70% $H_2$ in the gas-phase was measured. The reactor was heated to bring the methanogens into an active mode (see FIG. 8). Electrolysis was started for ~3.5 h. The next day we could detect methane with a final concentration of 18%.

Example 7

Figure 9:
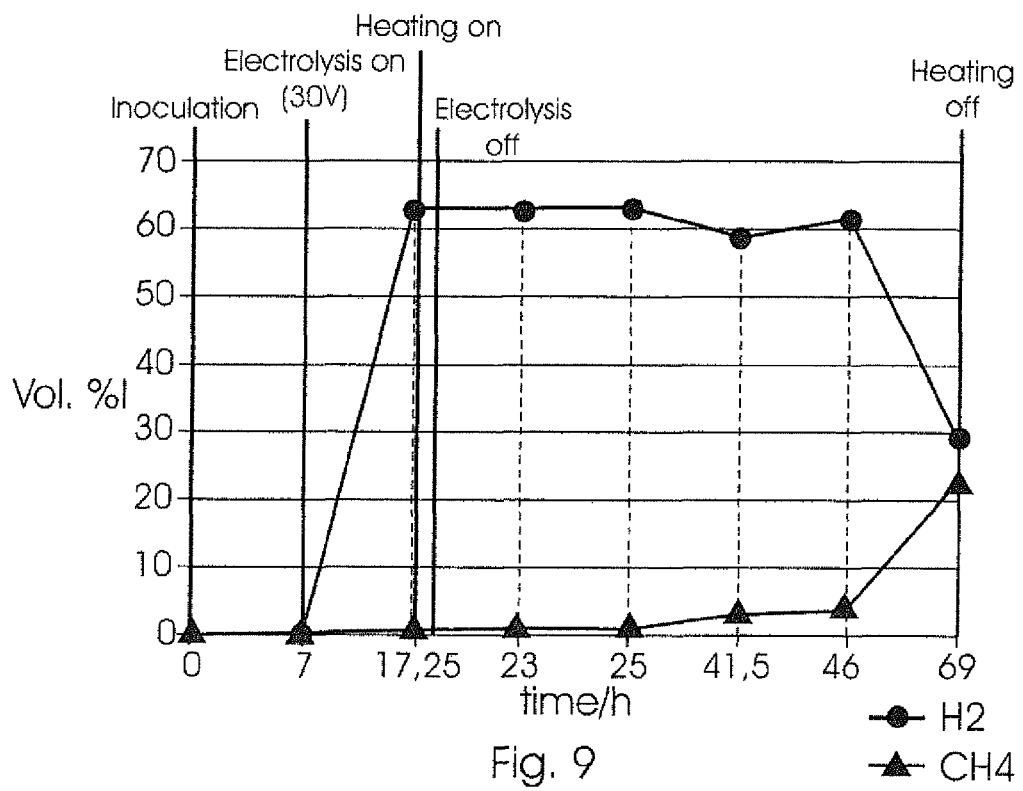
FIG. 9 is a graph showing the results of an experiment with *Mc, thermolithotrophicus*, 20 bar, 30 V, 65° C.

FFGF-reaction with *Mc. thermolithotrophicus* at 20 bar $CO_2$ and 30 V
Electrolyte cathode: 240 ml SME, pH 7
Electrolyte anode: $Mg_2SO_4$, 1.25 M
Inoculum: 60 ml liquid pre-culture
Gas-phase 20 bar $CO_2$
A time switch controlled the automatic start of the electrolysis at 22.00
Voltage 30 V
The results of this experiment are provided in FIG. 9.

This experiment was performed at 20 bar $CO_2$ with no additional hydrogen. Hydrogen was produced by electrolysis at 30 V which has been started automatically in the night at 22.00. At this stage the reactor was at room temperature. In the morning when electrolysis ran for 10.25 h~63% $H_2$ in the gas-phase was measured. Heating was switched on to activate the methanogens (see FIG. 9). The final methane concentration was ~22.5%.

Example 8

Figure 10:
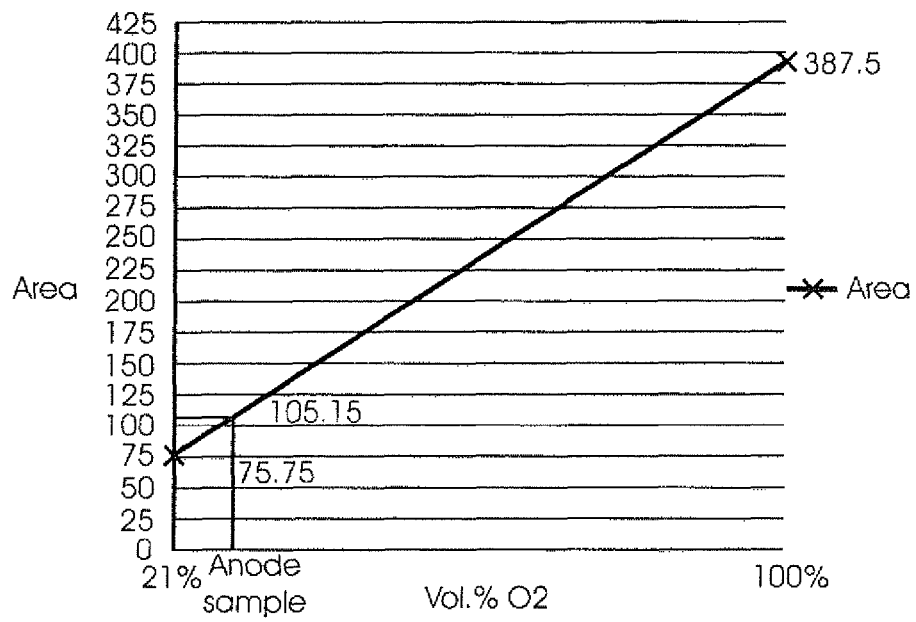
FIG. 10 is a graph showing the results of an experiment to show that oxygen is produced in the anode reaction vessel of the invention.

The gas at the anode was sampled and analyzed in the GC. With our GC machine detection of oxygen is possible (but not quantification; nitrogen as carrier gas is not suited for the quantification of oxygen). But, to roughly estimate the amount of oxygen produced at the anode a "calibration curve" with two standards (100% pure oxygen and air ~21% $O_2$) was made. The resulting peaks had different areas (at the same retention time). By plotting the area—which is direct proportional to the amount of gas injected-against the volume percentage we got the "calibration curve" (see FIG. 10). After injection of the "anode" sample with unknown composition we could roughly estimate the volume percentage of oxygen with corresponded to ~30% (Note that in this case electrolysis ran for ~13 h at 30 V). Although a calibration curve with only two measuring points and under given conditions (nitrogen gas as carrier) is inaccurate for an exact quantification we can say that the amount of oxygen in the anode is higher than that of the air. So it is proven that oxygen is being produced at the anode reactor.

Example 9

Figure 11:
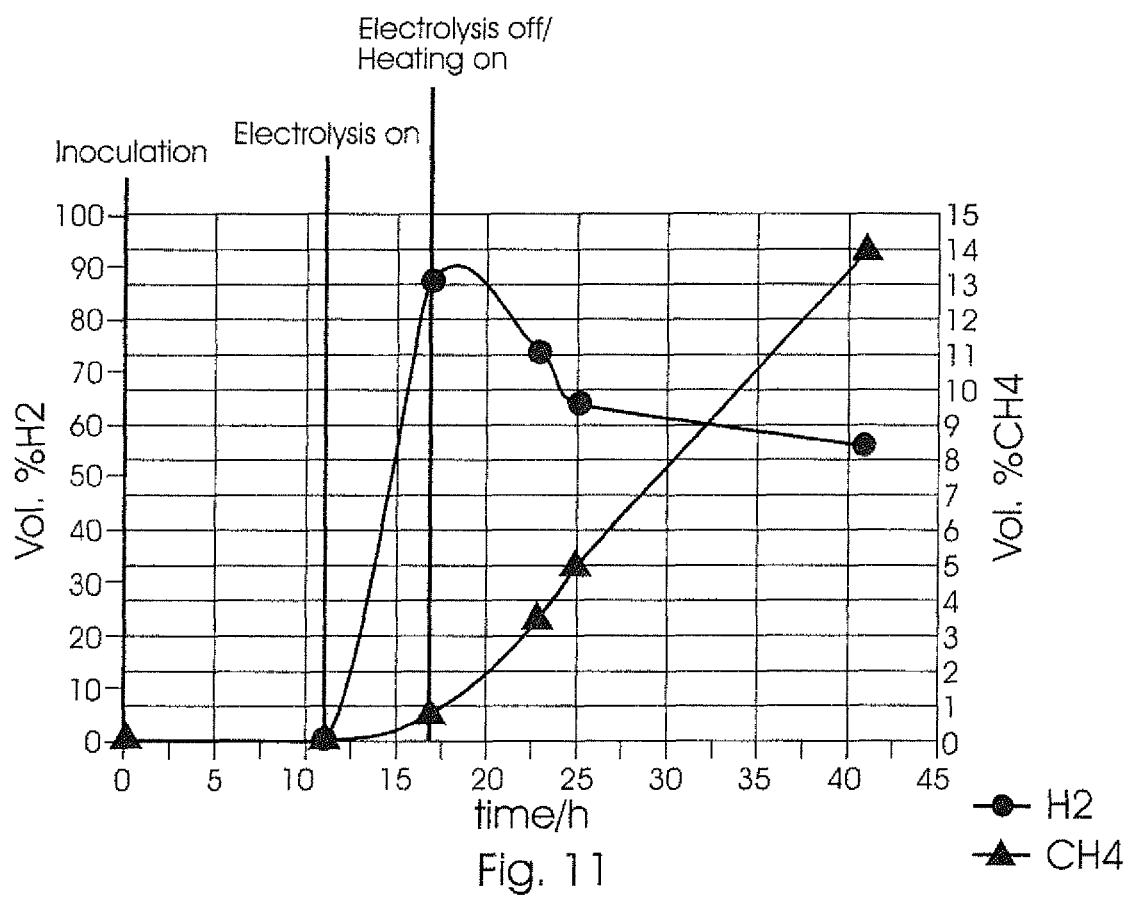
FIG. 11 is a graph showing the results of an experiment with *M. kandleri*, 10 bar, 30 V, 97° C.

*M. kandleri* (97° C.) at 10 bar $CO_2$ and 30 V, Inoculum with frozen cells
Electrolyte cathode: 280 ml SME, pH 6
Electrolyte anode: $Mg_2SO_4$, 1.25 M
Inoculum: 0.5 g frozen cells, resuspended in 20 ml SME under anaerobic conditions
Gas-phase 10 bar $CO_2$
Start electrolysis (30 V) at room temperature in the night per timer for 6 h
Start heating in the morning when enough hydrogen is present
15 ml gas sample taken, 5 ml discharged (dead volume), 10 ml used for analysis of 200 µl in duplicates
The results of this experiment are shown in FIG. 11.
This 10 bar $CO_2$ experiment with *M. kandleri* did produce methane. Frozen cells were used as inoculum and this was a successful approach. Electrolysis started at room temperature and produced ~85% hydrogen within 6 h. Within a day of incubation at 97° C. the methanogens produced 15 Vol. % of $CH_4$. Decided to use frozen *M. kandleri* cells for subsequent experiments.

Example 10

Figure 12:
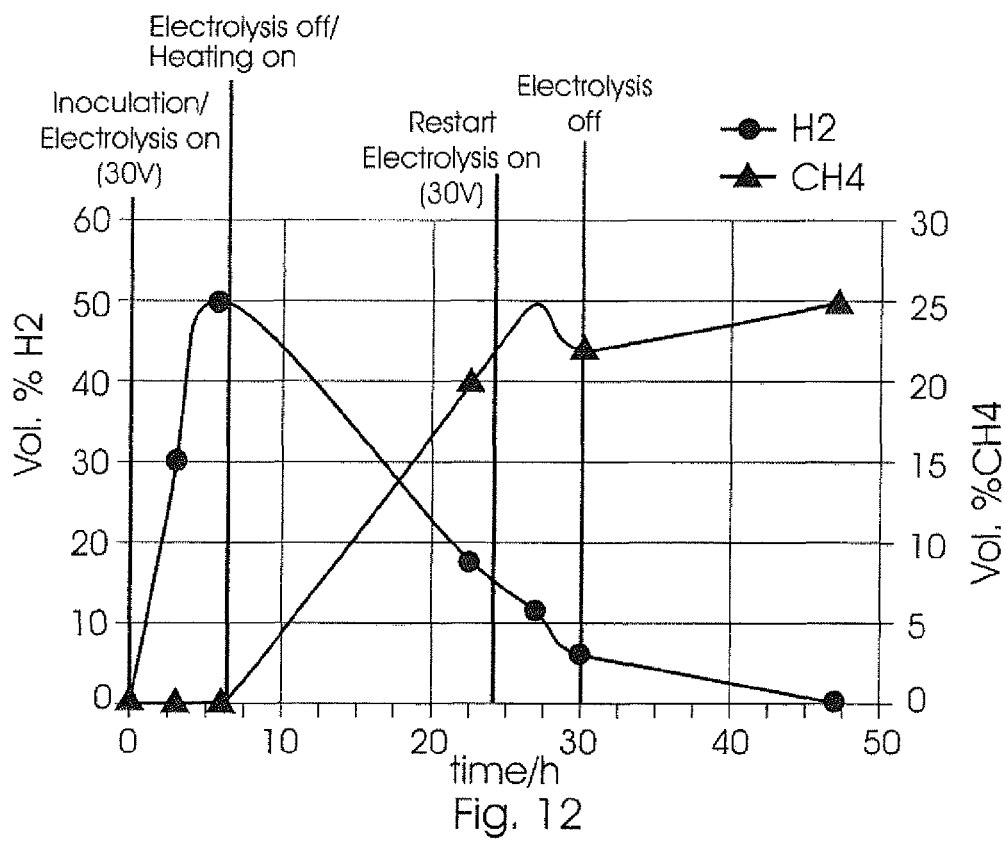
FIG. 12 is a graph showing the results of an experiment with *M. kandleri*, 20 bar, 30 V, 97° C.

*M. kandleri* (97° C.) at 20 bar $CO_2$ and 30 V, Inoculation with frozen cells
Electrolyte cathode: 280 ml SME, pH 6
Electrolyte anode: $Mg_2SO_4$, 125 M
Inoculum: 0.5 g frozen cells, resuspended in 20 ml SME under anaerobic conditions
Gas-phase 20 bar $CO_2$
Start electrolysis (30 V) immediately after inoculation
Start heating when enough hydrogen is produced from electrolysis
The results of this experiment are provided in FIG. 12.
In this experiment with 20 bar $CO_2$ we inoculated resuspended, frozen cells and immediately started electrolysis at room temperature. We stopped electrolysis in the evening after ~7 h and heated the reactor up (50% $H_2$ present). Overnight *M. kandleri* converted $H_2$ and $CO_2$ into ~25% methane. Then we restarted electrolysis but the current decreased rapidly to 0.07-0.01 A. After releasing the gas produced in the anode reactor (>200 ml) the current flow was immediately increasing but only for a short time. Interestingly, the percentages of $H_2$ and $CH_4$ in the cathode head-space also decreased after the release of the anode-gas. As the current flow was low we could not produce more $H_2$. The remaining $H_2$ (~6% in the evening) was completely converted into methane over night by active methanogens.

Example 11

Figure 13:
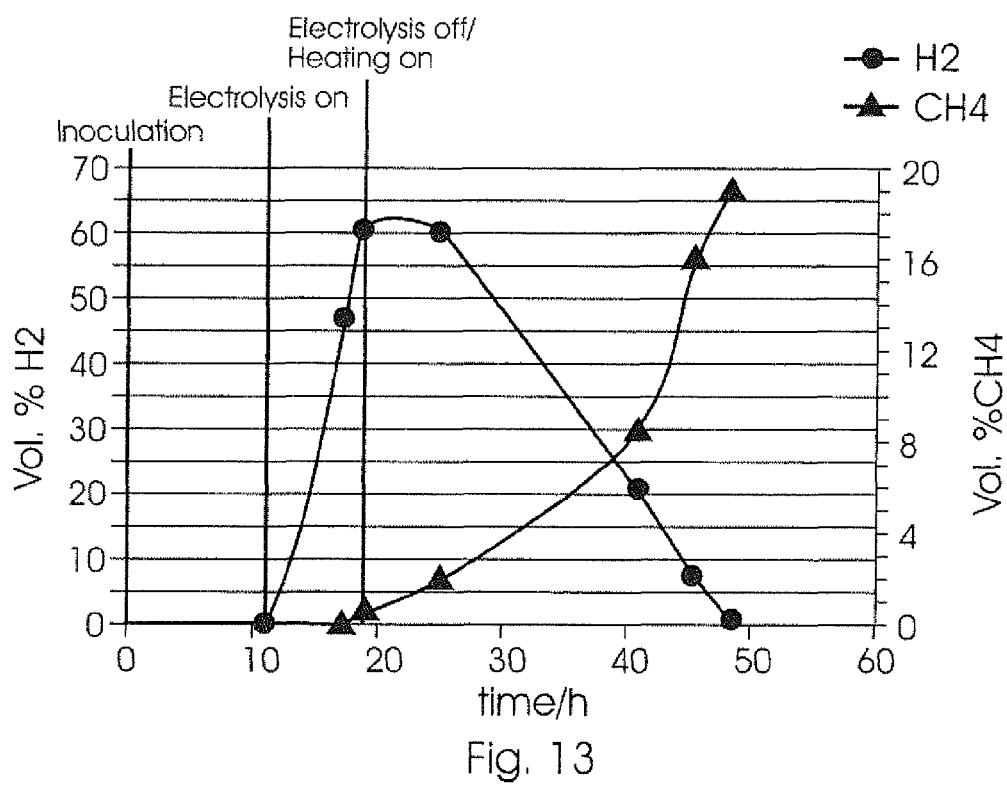
FIG. 13 is a graph showing the results of an experiment with *M. kandleri*, 20 bar, 30 V, 105° C.

*M. kandleri* (105.5° C.) at 20 bar $CO_2$ and 30 V, Inoculation with frozen cells
Electrolyte cathode: 280 ml SME, pH 6
Electrolyte anode: $Mg_2SO_4$, 1.25 M
Inoculum: 0.5 g frozen cells, resuspended in 20 ml SME under anaerobic conditions
Gas-phase 20 bar $CO_2$
Start electrolysis (30 V) at room temperature in the night per timer for 6 h
Start heating in the morning when enough hydrogen is present
15 ml gas sample taken, 5 ml discharged (dead volume), 10 ml used for analysis of 200 µl in duplicates
The results of this experiment are shown in FIG. 13.
In this experiment electrolysis was started at room temperature. Within 8 h 60% of hydrogen was produced from electrolysis (at initial 20 bar $CO_2$) which is enough to support the growth of the methanogens. Heating started at 10.00 the methanogens immediately started to produce methane so that we could measure 2% $CH_4$ in the evening (see FIG. 13). Within 24 h the methanogens converted all hydrogen into methane to a final concentration of 19%. If more hydrogen had been present the methanogens would have probably produced even more methane.

Example 12

Figure 14:
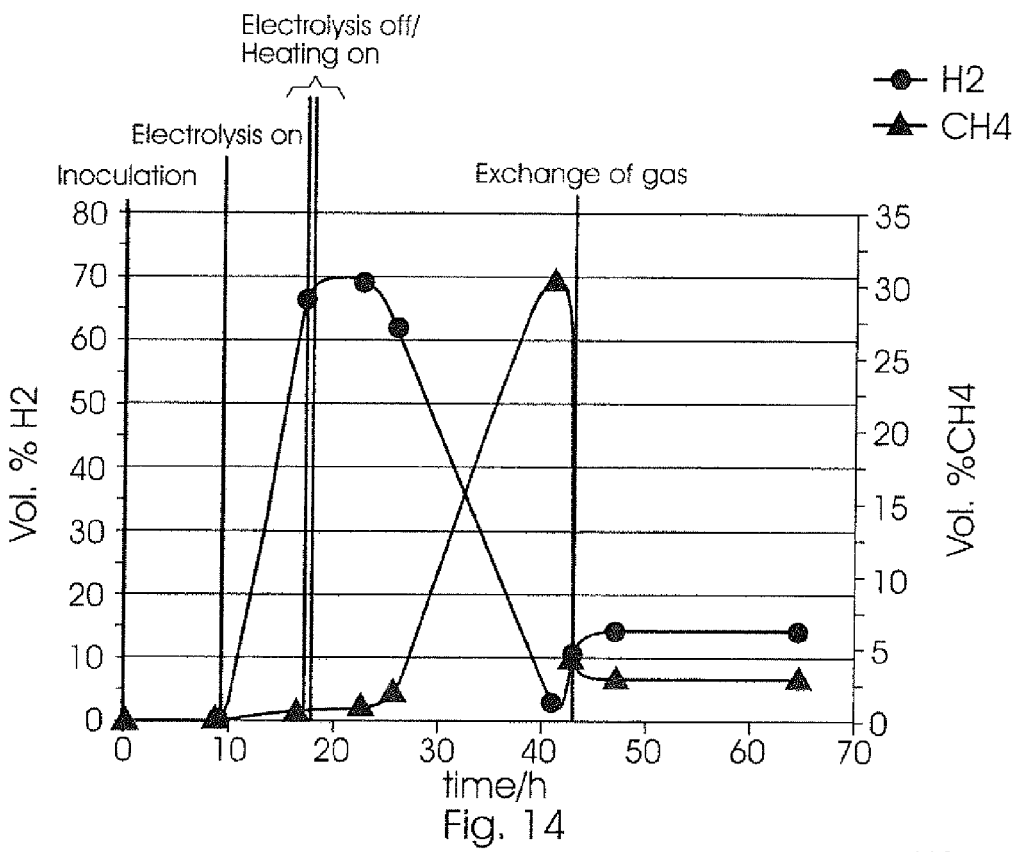
FIG. 14 is a graph showing the results of an experiment with *Mc. jannaschii* 10 bar, 30 V, 85° C.

*Mc. jannaschii* at 10 bar $CO_2$, 30 V and 85° C.
Electrolyte cathode: 240 ml medium, pH 6.5 and 60 ml liquid pre-culture
Electrolyte anode: $Mg_2SO_4$, 1.25 M
Initial Gas-phase 10 bar $CO_2$
Start electrolysis (30 V) at room temperature in the night per timer for 8 h
Measure hydrogen content in the morning and add additional hydrogen if necessary; then start heating
15 ml sample taken, 5 ml discharged (dead volume), 10 ml used for analysis of 200 µl in duplets
The results of this experiment are provided in FIG. 14.
Inoculated liquid pre-cultures and started with 10 bar $CO_2$. Electrolysis ran for 8 h at 30 V. After 22.5 h of incubation at the final temperature (85° C.) the methane concentration was ~30 Vol. % which corresponds to 244 ml methane in total. Then gas was released and external hydrogen added.

Example 13

Figure 15:
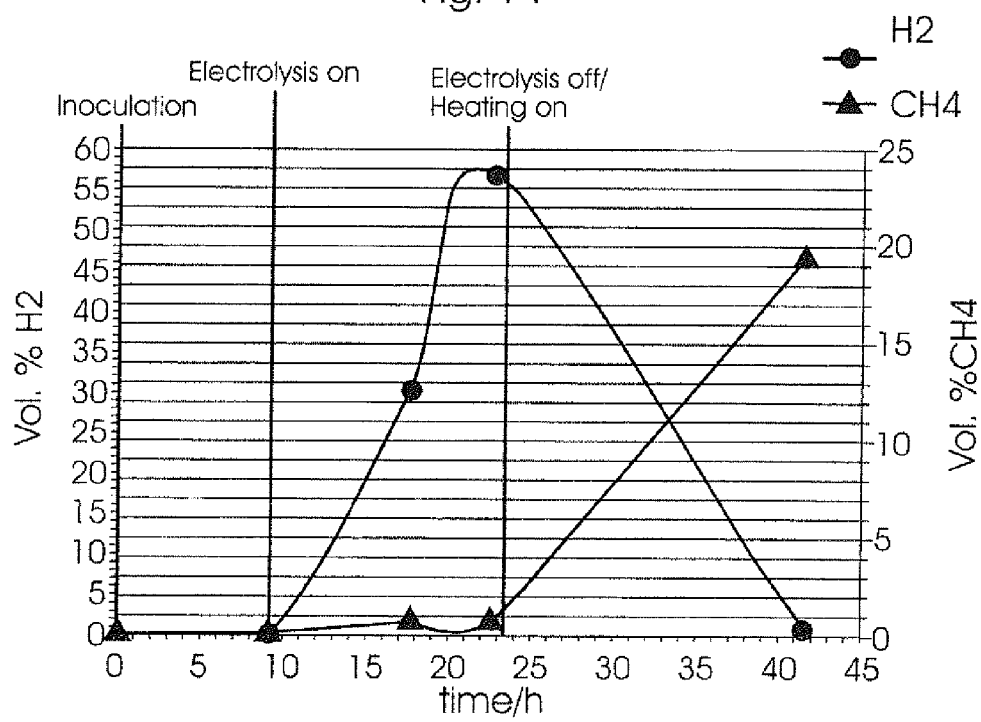
FIG. 15 is a graph showing the results of an experiment with *Mc. jannaschii* 10 bar, 30 V, 92° C.

*Mc. jannaschii* at 10 bar $CO_2$, 30 V and 92° C.
Electrolyte cathode: 280 ml medium, pH 6.5 and 0.5 g frozen cells, resuspended in 20 ml under anaerobic conditions
Electrolyte anode: $Mg_2SO_4$, 1.25 M
Initial Gas-phase 20 bar $CO_2$
Start electrolysis (30 V) at room temperature in the night per timer
Measure hydrogen content in the morning and add additional hydrogen if necessary; then start heating
15 ml sample taken, 5 ml discharged (dead volume), 10 ml used for analysis of 200 µl in duplets
The results of this experiment are shown in FIG. 15.
This test produced 19.5 vol. % in total without addition of external hydrogen (see FIG. 15). Within 41.5 h of total incubation time the methanogens converted all present hydrogen into methane.

Example 14

*Mc. jannaschii* at 20 bar $CO_2$, 30 V and 92° C.
Electrolyte cathode: 280 ml medium, pH 6.5 and 0.5 g frozen cells, resuspended in 20 ml under anaerobic conditions Electrolyte anode: Mg$_2$SO$_4$, 1.25 M Initial Gas-phase 20 bar CO$_2$ Start electrolysis (30 V) at room temperature in the night per timer Measure hydrogen content in the morning and add additional hydrogen if necessary; then start heating 15 ml sample taken, 5 ml discharged (dead volume), 10 ml used for analysis of 200 μl in duplets The results of this experiment are shown in FIG. 16.

Figure 16:
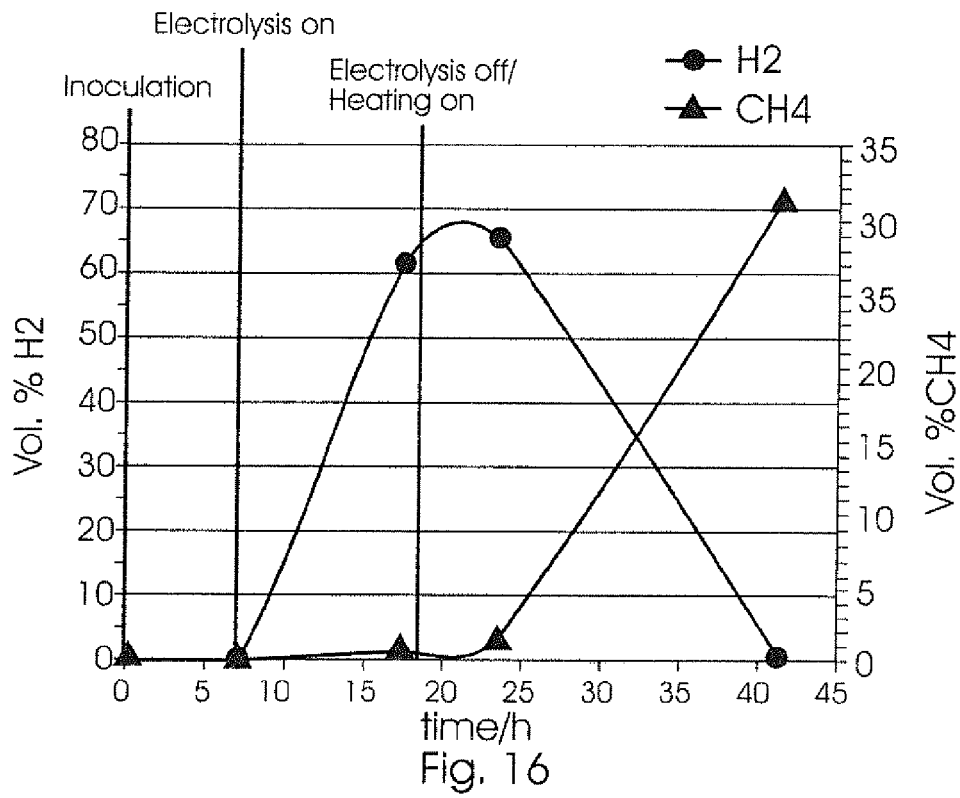
FIG. 16 is a graph showing the results of an experiment with *Mc. jannaschii* 20 bar, 30 V, 92° C.

This test produced 31 vol. % of methane which corresponds to 465 ml gaseous methane (see FIG. 16). No external hydrogen was added. All hydrogen present was produced from electrolysis and has been utilized by the methanogens for synthesis of methane.

Example 15

*Mc. jannaschii* at 92° C. with addition of external hydrogen at 30 bar H$_2$/CO$_2$ Electrolyte cathode: 280 ml medium, pH 6.5 and 0.5 g frozen cells, resuspended in 20 ml under anaerobic conditions Electrolyte anode: Mg$_2$SO$_4$, 1.25 M Initial Gas-phase 15 bar CO$_2$ and 15 bar external hydrogen=>30 bar H$_2$/CO$_2$ gas-phase with ~70/30 (v(v) H$_2$/CO$_2$ no electrolysis 15 ml sample taken, 5 ml discharged (dead volume), 10 ml used for analysis of 200 μl in duplets Determination of the time taken to convert all the hydrogen of methane Determination of the CH$_4$ production rate The results of this experiment are provided in FIG. 17.

Figure 17:
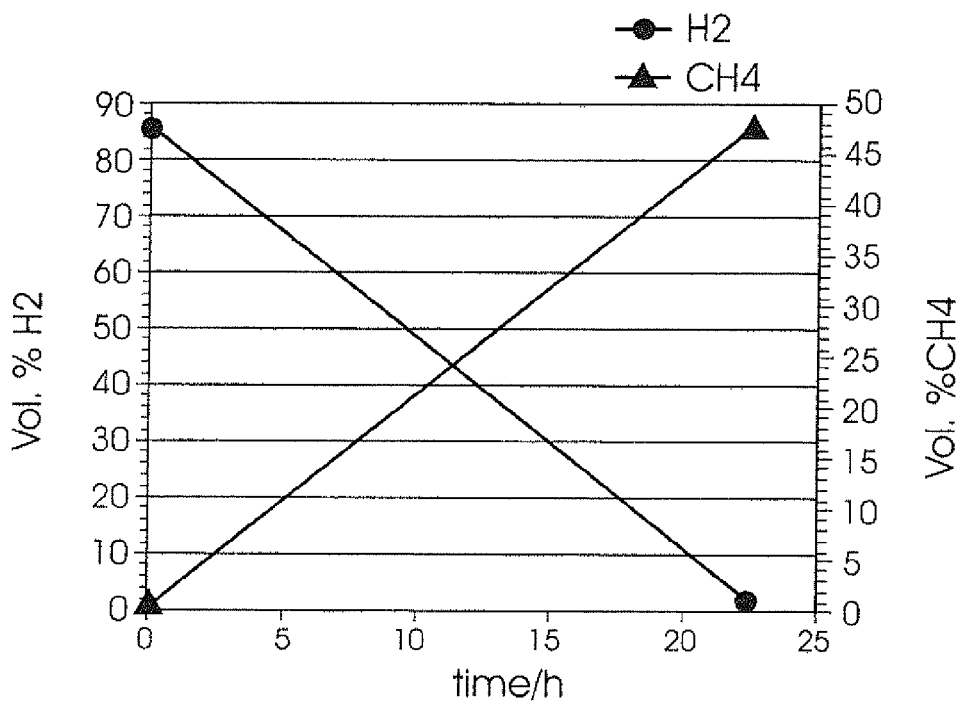
FIG. 17 is a graph showing the results of an experiment with *Mc. jannaschii* 30 bar, 92° C.

The experiment was started with an initial ratio of 80/20 (v/v) H$_2$/CO$_2$ (see FIG. 17). It took 22.5 h of incubation at the final temperature for *Mc. jannaschii* to consume (nearly) all the hydrogen present. The total amount of methane was ~48 vol. % which corresponds to 1425 ml methane. The methane production rate for this experiment was 63 ml/h. The pH stayed constant at 6.5.

The invention claimed is:

1. A method for producing methane from carbon dioxide, hydrogen and anaerobic Archaea methanogens provided in an aqueous growth substrate comprising:
    supplying the aqueous growth substrate containing the anaerobic Archaea methanogens to a reaction vessel; and
    pressurizing the vessel containing the aqueous growth substrate to a pressure of from 5 to 1000 bar with a pressurizing fluid consisting of carbon dioxide, or a mixture of carbon dioxide and hydrogen.

2. The method claimed in claim 1, wherein the vessel and aqueous growth substrate is pressurized to a pressure of 5 to 500 bar.

3. The method claimed in claim 2, wherein the vessel and aqueous growth substrate is pressurized to a pressure of from 10 to 150 bar.

4. The method claimed in claim 3, wherein the vessel and aqueous growth substrate is pressurized to a pressure of from 40 to 150 bar.

5. The method claimed in claim 1, wherein sufficient aqueous growth substrate is provided in the reaction vessel to provide an aqueous growth substrate to head space volumetric ratio of 1:1 to 4:1.

6. The method claimed in claim 5, wherein the volumetric ratio of aqueous growth substrate to head space is from 2:1 to 3:1.

7. The method claimed in claim 1, wherein the aqueous growth substrate is pressurized with a mixture of hydrogen and carbon dioxide.

8. The method claimed in claim 7, wherein the hydrogen and carbon dioxide are present in a molar ratio of 4:1 to 1:4.

9. The method claimed in claim 8, wherein the hydrogen and carbon dioxide are present in a molar ratio of 1:1 to 1:4.

10. The method claimed in claim 9, wherein the hydrogen and carbon dioxide are present in a molar ratio of 1:2 to 1:4.

11. The method claimed in claim 1, wherein the pH of the aqueous growth medium is maintained in the range from 6 to 7.5.

12. The method claimed in claim 11, wherein the pH of the aqueous growth medium is maintained in the range from 6.5 to 7.

13. The method claimed in claim 1, wherein the reaction is carried out at a temperature at or near the optimum for growth of the methanogens.

14. The method claimed in claim 13, wherein the methanogens are a hyperthermophilic/hyperextremophile anaerobic Archaea, and wherein the reaction is carried out at a temperature of 50° C. to 400° C.

15. The method claimed in claim 13, wherein the methanogens is/are a psychrophile/cryophile anaerobic Archaea, and wherein the reaction is carried out at a temperature of −50 to 50° C.

16. The method claimed in claim 1, wherein pH of the aqueous growth medium is controlled.

17. The method claimed in claim 16, wherein the pH of the aqueous growth medium is controlled by providing a cathode in the reaction vessel and passing a current through the aqueous growth medium to generate hydrogen and further to control the pH with electrolysis.

18. The method claimed in claim 17, wherein electrolysis is implemented intermittently to control the pH.

19. A method for the production of methane from carbon dioxide, hydrogen and anaerobic Archaea methanogens includes the steps of:
    a) providing an anode reaction vessel (14) containing a positive electrode (anode) and a liquid electrolytic medium comprising water and ionizing material;
    b) providing a cathode reaction vessel (12) containing a negative electrode (cathode), an electrolytic aqueous growth substrate, methanogens, carbon dioxide and hydrogen, wherein the cathode vessel (12) and aqueous growth substrate is pressurized to a pressure of from 5 to 1000 bar;
    c) connecting the first and second reaction vessels with connection means which allows electrons and/or ions, to pass between the electrolytic media of the anode and cathode reaction vessels;
    d) applying a direct electrical current to the positive electrode and the negative electrode to:
        effect ionization of hydrogen in the cathode reaction vessel (12) to produce hydrogen and also to increase the pH of the electrolytic aqueous growth substrate; and
        effect ionized oxygen in the first reaction vessel (14), to form oxygen.

20. The method claimed in claim 19, wherein electrolysis is implemented intermittently to control the pH in the cathode reaction vessel (12).

21. The method claimed in claim 19, wherein reaction vessels (12) and (14) are operated at the same internal pressure.

22. The method claimed in claim 19, wherein the connection means is an electrolytic medium, a membrane which allows electrons to pass through, and possibly some ions, is provided, and the connection means is provided with a valve that is insulated from the electrolyte.

23. The method claimed in claim 19, wherein the reaction vessels are operated at different temperature.

24. The method claimed in claim 23, wherein the anode reaction vessel (14) is operated at ambient temperature; and the cathode reaction vessel (12) is operated at a temperature at or near the optimum for growth of the methanogens.

25. The method claimed in claim 24, wherein the methanogens are a hyperthermophilic hyperextremophile anaerobic Archaea, and wherein the reaction is carried out at a temperature of 50° C. to 400° C.

26. The method claimed in claim 24, wherein the methanogens are a psychrophile/cryophile anaerobic Archaea, and wherein the reaction is carried out at a temperature of −50 to 50° C.

27. The method claimed in claim 19, wherein the cathode reaction vessel (12) and the anode reaction vessel (14) are pressurized to a pressure of 5 to 500 bar.

28. The method claimed in claim 27, wherein the cathode reaction vessel (12) and the anode reaction vessel (14) are pressurized to a pressure of from 10 to 150 bar.

29. The method claimed in claim 28, wherein the cathode reaction vessel (12) and the anode reaction vessel (14) are pressurized to a pressure of from 40 to 150 bar.

30. The method claimed in claim 19, wherein cathode reaction vessel (12) is pressurized with a pressurizing fluid consisting of a mixture of hydrogen and carbon dioxide.

31. The method claimed in claim 30, wherein the hydrogen and carbon dioxide are present in a molar ratio of 4:1 to 1:4.

32. The method claimed in claim 31, wherein the hydrogen and carbon dioxide are present in a molar ratio of 1:1 to 1:4.

33. The method claimed in claim 32, wherein the hydrogen and carbon dioxide are present in a molar ratio of 1:2 to 1:4.

34. The method claimed in claim 19, wherein sufficient aqueous growth substrate is provided in the cathode reaction vessel (12) to provide an aqueous growth substrate to head space volumetric ratio of 1:1 to 4:1.

35. The method claimed in claim 34, wherein the volumetric ratio of aqueous growth substrate to head space is from 2:1 to 3:1.

36. The method claimed in claim 19, wherein the pH of the aqueous growth medium is maintained in the range from 6 to 7.5.

37. The method claimed in claim 36, wherein the pH of the aqueous growth medium is maintained in the range from 6.5 to 7.

38. An apparatus for the production of methane from carbon dioxide, hydrogen and anaerobic Archaea methanogens comprising:
   a cathode reaction vessel (12) for containing carbon dioxide and electrolytic water;
   an anode reaction vessel (14) for containing electrolytic water;
a negative electrode (cathode) capable of supporting anaerobic Archaea methanogens located within the cathode reaction vessel (12);
a positive electrode (anode) located within the anode reaction vessel (14); and
connection means for connecting electrolytic water in the cathode reaction vessel (12) and anode reaction vessel (14) so that a direct electric current can flow between the two,
characterized in that the cathode reaction vessel (12) and the anode reaction vessel (14) are adapted to be pressurized to a pressure of from 5 to 1000 bar, the cathode reaction vessel (12) is adapted to be pressurized with a pressurizing fluid consisting of carbon dioxide or a mixture of carbon dioxide and hydrogen, and internal surfaces of cathode reaction vessel (12) and anode reaction vessel (14) are made from non-conductive non-corrosive materials that insulate the electrolytic media from the rest of the apparatus, except for the cathode and anode which come in to contact with electrolytic water within the reaction vessels.

39. The apparatus claimed in claim 38, wherein the connection means is a conduit containing liquid electrolyte, the conduit includes a semi-pervious membrane which allows the passage of ions between the electrolytic water in the cathode reaction vessel (12) and anode reaction vessel (14) and the conduit has a valve which does not make electrical contact with the electrolyte.

40. The apparatus claimed in claim 38, including means for equalizing the pressure in the cathode reaction vessel (12) and anode reaction vessel (14), wherein the pressure equalizing means is pressurized by pressurizing fluid used to pressurize the cathode reaction vessel (14), which also simultaneously pressurizes the anode reaction vessel (12), and wherein the pressure equalizing means provides electrical insulation between the cathode reaction vessel (12) and anode reaction vessel (14).

41. The apparatus claimed in claim 40, wherein the pressure equalizing means comprises a non-conductive tube with a piston located therein, and an indicator for indicating the position of the piston within the tube.

* * * * *